US005616557A

United States Patent [19]
Tsuchiya et al.

[11] Patent Number: 5,616,557
[45] Date of Patent: Apr. 1, 1997

[54] PROCESS FOR SELECTIVELY INHIBITING ACTIVITY OF ENDOTOXIN

[75] Inventors: Masakazu Tsuchiya; Kazuaki Harada, both of Amagasaki, Japan

[73] Assignee: Wako Pure Chemical Industries, Ltd., Osaka, Japan

[21] Appl. No.: 454,866

[22] Filed: May 31, 1995

Related U.S. Application Data

[63] Continuation of Ser. No. 183,436, Jan. 19, 1994, abandoned.

[30] Foreign Application Priority Data

Jan. 21, 1993 [JP] Japan .................................. 5-026159

[51] Int. Cl.$^6$ .................................................. A61K 38/12
[52] U.S. Cl. ......................... 514/11; 514/2; 514/9; 514/21; 530/317
[58] Field of Search ............................. 514/2, 9, 11, 21; 530/317

[56] References Cited

U.S. PATENT DOCUMENTS

| | | | |
|---|---|---|---|
| 4,276,050 | 6/1981 | Finca et al. | 436/825 |
| 4,808,314 | 2/1989 | Karplus et al. | 210/638 |
| 5,068,314 | 11/1991 | Nakamura et al. | 530/317 |
| 5,177,059 | 1/1993 | Handley et al. | 514/8 |
| 5,198,339 | 3/1993 | Hansen et al. | 435/7.2 |
| 5,316,911 | 5/1994 | Baek et al. | 435/7.9 |

FOREIGN PATENT DOCUMENTS

| | | |
|---|---|---|
| 0491047 | 6/1992 | European Pat. Off. . |
| 0549102 | 6/1993 | European Pat. Off. . |
| 56-48897 | 5/1981 | Japan . |
| 58-13519 | 1/1983 | Japan . |
| 59-67210 | 4/1984 | Japan . |
| 184100 | 9/1985 | Japan . |
| 0049304 | 1/1992 | Japan . |
| 2080524 | 3/1982 | United Kingdom . |

OTHER PUBLICATIONS

Database WPI, Week 9248, Derwent Publications Ltd. London, GB; AN 92–390496 abstract of CA–A–2 037 727; 8 Sep. 1992.

Database WPI, Week 9039, Derwent Puhblications Ltd. London, GB; AN 92–390496 abstract of JP–A–2 207 098; 16 Aug. 1990.

Patent Abstracts of Japan, vol. 14, No. 376 (P–1092) 14 Aug. 1990; abstract of JP–A–02 141 666 (Wako Pure Chem Ind Ltd) 31 May 1990.

Biochemical and Biophysical Research Communications, vol. 101, No. 2; 30 Jun. 1981, pp. 434–439; A. Kakinuma et al.

FEBS Letters, vol. 129, No. 1, 29 Jun. 1981; pp. 318–321; T. Morita et al.

Karplus et al, Journal of Immunological Methods, vol. 105, pp. 211–220.

*Primary Examiner*—Howard E. Schain
*Attorney, Agent, or Firm*—Armstrong, Westerman, Hattori, McLeland & Naughton

[57] ABSTRACT

By contacting a peptide derivative or a protein having a property of binding to endotoxin (ET) to inhibit the activity of ET, and at least one surfactant with a sample containing ET, the activity of ET can be inhibited, and even when an ET analogous substance having ET activity is present in the thus treated sample, it can be measured without influence of ET.

6 Claims, 4 Drawing Sheets

PROCESS FOR SELECTIVELY INHIBITING ACTIVITY OF ENDOTOXIN

This application is Continuation application of Ser. No. 08/183,436 filed Jan. 19, 1994, now abandoned.

BACKGROUND OF THE INVENTION

This invention relates to a process for selective inhibition of properties of endotoxin (hereinafter abbreviated as "ET"), such as a property of reacting with horseshoe crab hemocyte lysate (hereinafter abbreviated as "AL solution") to cause activation reaction of an enzyme (e.g. protease) contained in said solution (hereinafter abbreviated as "enzyme activation reaction") or gelation reaction; and a process for measuring at least one substance other than ET among substances having ET activity (hereinafter abbreviated as "activating substances for AL solution") (the substance other than ET is hereinafter abbreviated as "ET analogous substance") which is contained in a sample treated by the above inhibiting process.

ET's are lipopolysaccharides (LPS) present in cell walls of Gram-negative bacteria and are known as potent pyrogens. Therefore, the detection of ET in parenteral drugs and the like is considered important, and test methods for endotoxin are described in the U.S. Pharmacopoeia and the Japanese Pharmacopoeia. ET is considered a main cause of shock in Gram-negative bacterial infections. In clinical diagnoses, the measurement of endotoxin in plasma is employed, for example, for diagnoses of Gram-negative bacterial infections, judgement of curative effect on and prognosis of Gram-negative bacterial infections, and early diagnosis of endotoxin shock. AL solution has a property of being activated by ET to cause activation reaction of an enzyme (e.g. protease) or gelation reaction. Simple, low-cost ET detecting methods utilizing this property, for example, so-called Limulus test including a method of measuring the degree of activation of the enzyme (e.g. protease) by a colorimetric method, or utilizing the gelation reaction (in the present invention, the "Limulus test" includes these methods mentioned above) are widely employed in the fields of medical science, pharmacy and microbiology.

Reagents used for the Limulus test, however, have been disadvantageous in that since they react also with an ET analogous substance(s) such as (1→3)-β-D-glucan and/or a derivative thereof (hereinafter abbreviated as "βG") [Kakinuma et al., Biochem. Biophys. Res. Commun., vol. 101, 434–439 (1981), and Morita et al., FEBS Lett., vol. 129, 318–321 (1981)], the presence of βG together with ET in a sample for measurement causes positive errors in measured values.

Although, βG's are interfering substances which cause positive errors in ET measurement, the detection of βG by use of AL solution is considered utilizable for diagnoses of infectious diseases caused by Eumycetes, because they are components of cell wall of Eumycetes such as yeast and mold. Hence the development of a method for measurement of βG is investigated. However, since commercially available reagents usable for the Limulus test, of course, react with ET, there has been a problem in that when βG is measured using the reagents, ET in a sample affects measured values.

For solving the above problems, there have been reported, for example, a process for removing a factor which is present in AL solution and reacts with ET to cause activation reaction of an enzyme (e.g. protease) or gelation reaction (hereinafter abbreviated as "ET-sensitive factor"), by treating AL solution by various chromatographies (Japanese Patent Unexamined Publication (JP-A) No. 59-27828, JP-A H2-138193 and JP-A H4-76459), a process for inhibiting ET-sensitive factors by adding a peptide having affinity for ET to AL solution (JP-A H2-207098), and a process for inhibiting ET-sensitive factors by adding antibodies against ET-sensitive factor to AL solution (JP-A H4-52558). All of these processes, however, are disadvantageous in that since they comprise treating AL solution itself, there is a strong fear that during the treatment, AL solution may be contaminated with ET or βG, which are widely present in a usual environment. Moreover, these processes require sterile facilities and complicated sterile operations for avoiding the contamination, and the peptide having affinity for ET and the antibodies against ET-sensitive factor are difficult to obtain and are expensive. As is clear from these facts and the like, the processes involve many economical and technical problems.

For inactivating ET by treatment of not AL solution but a sample for measurement, a process for heat-treating the sample has been reported (JP-A H2-141666). This process is free from the defects of the processes described above, but is disadvantageous in that a long treatment time is required for sufficient inactivation of ET. Therefore, it cannot be said to be a preferable process.

SUMMARY OF THE INVENTION

This invention was made in consideration of such conditions and is intended to provide a process for selective inhibition of ET activity which can be practiced by easy operations by use of easily available reagents; a process for measuring at least one ET analogous substance in a sample by employing this inhibiting process; and a reagent for this measurement.

This invention provides a process for inhibiting the activity of ET which comprises contacting a peptide derivative or a protein, which has a property of binding to ET to inhibit the activity of ET (hereinafter abbreviated as "ET-inhibiting peptide") and at least one surfactant with a sample containing ET.

This invention also provides a process for measuring at least one ET analogous substance present in a sample which comprises reacting the sample treated by the above-mentioned inhibiting process with AL solution, and measuring the activity of an enzyme activated by enzyme activation reaction caused by the above reaction, or measuring the degree of turbidity change or gelation of the reaction solution which is due to gelation reaction caused by the above reaction, by means of a measuring instrument or with the naked eye.

In addition, this invention provides a pretreating solution for inhibiting the activity of ET which is an aqueous solution containing an ET-inhibiting peptide and at least one surfactant, does not react with AL solution, and neither inhibits nor enhance the reaction of AL solution with an ET analogous substance.

Further, this invention provides a reagent for measuring at least one ET analogous substance which comprises an ET-inhibiting peptide, at least one surfactant and AL solution.

DESCRIPTION OF THE PREFERRED EMBODIMENTS

Figure 1:
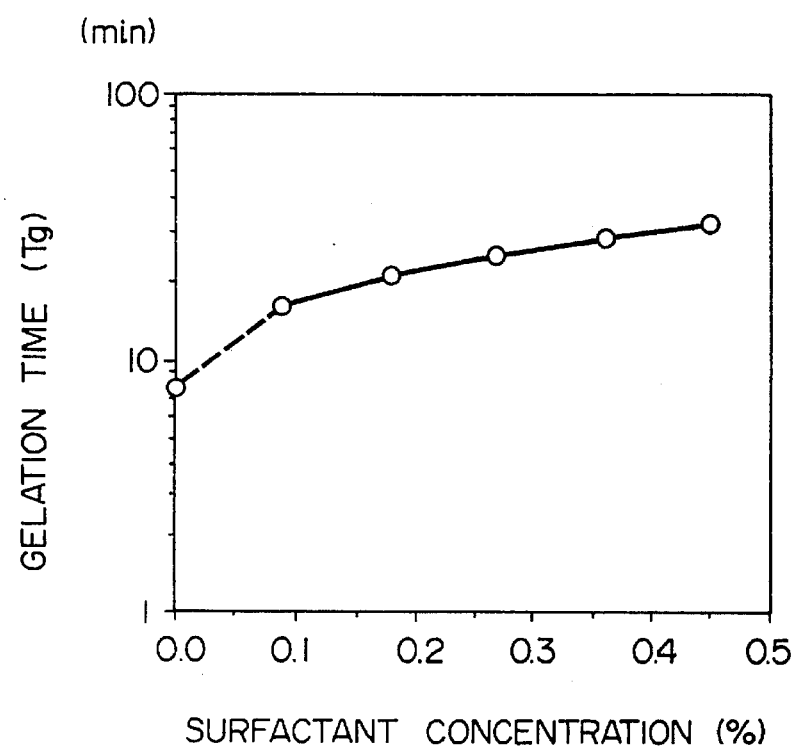
FIG. 1 is a graph showing the influence of the concentration of a surfactant on the measurement of endotoxin (hereinafter abbreviated as "ET") (*E. coli* 055:B5 LPS) in plasma, which was obtained in Example 1.

In the course of earnest study for finding a process for specific measurement of an AL solution activating substance such as ET, βG, etc. by use of AL solution, the present inventors found that the presence of both a surfactant and an ET-inhibiting peptide in a sample or a reaction solution obtained at the time of measuring the AL solution activating substance inhibits only the activity of ET contained in the sample or the reaction solution and permits specific detection of an ET analogous substance such as βG, whereby this invention has been accomplished.

In detail, it has been well known that surfactants and ET-inhibiting peptides represented by polymyxin and the like have a property of inhibiting ET activity. But, for inhibiting ET activity completely by using a surfactant or an ET-inhibiting peptide alone, the addition of a large amount of the surfactant or the ET-inhibiting peptide has been necessary. Therefore, there has been a problem in that when an ET analogous substance in a sample treated using either the surfactant or the ET-inhibiting peptide alone is measured by the Limulus test, influences such as inhibition of activation of enzymes in AL solution are brought about, so that no exact measured value can be obtained. However, the present inventors found that simultaneous use of a surfactant and an ET-inhibiting peptide permits complete inhibition of ET activity in a sample even when they are added in such an amount that they do not affect the Limulus test, whereby this invention has been accomplished.

The surfactant used in this invention is not critical so long as it neither inhibits nor enhance the activation reactions (enzyme activation reaction, gelation reaction, etc.) of AL solution by ET analogous substances and it does not cause appearance of non-specific turbidity during the reactions.

Specific examples of the surfactant are nonionic surfactants such as polyoxyethylene alkyl ethers (e.g. polyoxyethylene cetyl ether, polyoxyethylene lauryl ether, etc.), polyoxyethylene alkylphenyl ethers (e.g. polyoxyethylene octylphenyl ether, polyoxyethylene nonylphenyl ether, etc.), polyoxyethylene alkyl esters (e.g. polyoxyethylene sorbitan monooleate, polyoxyethylene sorbitan monopalmitate, polyoxyethylene sorbitan monostearate, polyoxyethylene sorbitan triolate, etc.), methylglucamide derivatives (e.g. octanoyl-N-methylglucamide, nonanoyl-N-methylglucamide, decanoyl-N-methylglucamide, etc.), alkyl sugar derivatives (e.g. n-octyl-β-D-glucoside, etc.) and the like; anionic surfactants such as sodium dodecyl sulfate (SDS), laurylbenzenesulfonic acid, deoxycholic acid, cholic acid, tris(hydroxymethyl)aminomethane dodecyl sulfate (Tris DS) and the like; cationic surfactants such as alkylamine salts (e.g. octadecylamine acetic acid salt, tetradecylamine acetic acid salt, stearylamine acetic acid salt, laurylamine acetic acid salt, lauryldiethanolamine acetic acid salt, etc.), quaternary ammonium salts (e.g. octadecyltrimethylammonium chloride, dodecyltrimethylammonium chloride, cetyltrimethylammonium chloride, cetyltrimethylammonium bromide, allyltrimethylammonium methylsulfate, benzalkonium chloride, tetradecyldimethylbenzylammonium chloride, octadecyldimethylbenzylammonium chloride, lauryldimethylbenzylammonium chloride, etc.), alkylpyridinium salts (laurylpyridinium chloride, stearylamidomethylpyridinium chloride, etc.) and the like; amphoteric surfactants such as 3-[(3-cholamidoamidopropyl)dimethylammonio]-1-propane sulfonate, 3-[(3-cholamidoamidopropyl)dimethylammonio]-2-hydroxy-1-propane sulfonate and the like; and natural surfactants such as saponin (derived from soybean), digitonin and the like. In view of influences on enzyme systems and the like during the reaction, the nonionic surfactants or the amphoteric surfactants are preferable. The above-exemplified surfactants may be used singly or in proper combination of two or more thereof.

Although their using concentration is varied depending on their kind and a sample to be treated, it may be chosen without particular limitation so long as it is a concentration at which ET activity can be sufficiently inhibited in the presence of an ET-inhibiting peptide and the reactivity of ET analogous substances such as βG with AL solution is neither enhanced nor inhibited. More specifically, the concentration of the surfactants in an ET-containing sample or a reaction solution of said sample with AL solution is properly chosen usually in the range of 0.005 to 5 w/v %, preferably 0.05 to 2.5 w/v %, more preferably 0.1 to 1 w/v %.

The ET-inhibiting peptide used in this invention is not critical so long as it is a peptide derivative (or a protein) which has a property of binding to ET to inhibit the activity of ET. The ET-inhibiting peptide preferably has properties of having strong basicity and/or having hydrophobic moieties. Preferable examples of the ET-inhibiting peptide are polymyxin produced by *Bacillus polymyxa* or the like, and tachyplesin, polyphemusin, anti-LPS factor and the like which are derived from AL solution. Since tachyplesin, polyphemusin, anti-LPS factor and the like are usually difficult to obtain and expensive, employment of polymyxin is economically advantageous. The polymyxin is not particularly limited and polymyxins A, B, C, D, E, K, M, P and the like may be used as a single purified component, a mixture of two or more of them, or a salt of any of them. Sulfate of polymyxin B is preferable in view of commercial availability.

Although the using concentration of the ET-inhibiting peptide is varied depending on the kind of the ET-inhibiting peptide and a sample to be treated, it may be chosen without particular limitation so long as it is a concentration at which ET activity can be sufficiently inhibited in the presence of the surfactant(s) and the reactivity of ET analogous substances such as βG with AL solution is neither enhanced nor inhibited. More specifically, the concentration of the ET-inhibiting peptide in an ET-containing sample or a reaction solution of said sample with AL solution is properly chosen usually in the range of 0.00001 to 0.1 w/v %, preferably 0.0001 to 0.05 w/v %, more preferably 0.001 to 0.01 w/v %.

The inhibiting process of this invention is practiced, for example, as follow.

The word "contacting" means that the endotoxin-inhibiting peptide and surfactant contact with an ET-containing sample by means of addition, dilution, stirring, mixing, vibration, etc. For example, it is sufficient that the above-exemplified surfactant(s) and ET-inhibiting peptide are present in an ET-containing sample or at the time of the reaction of said sample with AL solution, at concentrations in the above-mentioned ranges. Needless to say, when an ET analogous substance is measured in a sample treated by the inhibiting process of this invention, the concentrations of the surfactant(s) and the ET-inhibiting peptide at the time of the reaction of said sample and AL solution may be below the above-mentioned ranges.

When the inhibiting process of this invention is employed for inhibiting ET activity in a sample which may be heated, the ET activity can be more efficiently inhibited by employing heat treatment together with the inhibiting process. Particularly when an ET analogous substance in a sample containing inhibiting factors or the like, such as plasma or serum is measured by the Limulus test, it is preferable to employ heat treatment together with the inhibiting process as a pretreatment for removing the influences of the inhibiting factors or the like. Although the heat treatment may be carried out before or after the addition of both the surfactant(s) and the ET-inhibiting peptide, it is preferably carried out after the addition because a larger effect can be often obtained. Although not critical, the heating temperature in the heat treatment is usually 60°–220° C., preferably approximately 70°–100° C. Although not critical, the heating time is usually 3–60 minutes, preferably approximately 5–15 minutes. Any heating method may be employed so long as it permits heating of the sample under the above heating conditions. Preferable examples of heating method are heating in an incubator and heating in an autoclave.

For placing both the surfactant(s) and the ET-inhibiting peptide in an ET-containing sample or at the time of the reaction of said sample with AL solution, any method may be employed so long as it is such that the surfactant(s) and the ET-inhibiting peptide are added to said sample or AL solution to adjust their concentrations to values in the above-mentioned ranges before initiation of the activation of AL solution by ET. The following methods can be exemplified.

1) A method in which an ET-containing sample is properly diluted with a solution containing proper amounts of the surfactant(s) and the ET-inhibiting peptide (or a solution containing a proper amount of the surfactant(s) and a solution containing a proper amount of the ET-inhibiting peptide) which does not activate AL solution and neither inhibits nor enhance the reaction of AL solution with an ET analogous substance.

2) A method in which when an ET analogous substance is measured, proper amounts of the surfactant(s) and the ET-inhibiting peptide are previously incorporated into AL solution, and the thus treated AL solution is properly mixed with a sample for measurement.

When the above method 1) is employed, the degree of dilution of the sample is not critical, but when the sample is plasma or the like, the following problems are caused in some cases. When the degree of dilution is too low, an increase in viscosity or the formation of a precipitate is caused in the diluted plasma by denaturation of plasma protein during heating. When the degree of dilution is too high, proper detection of ET becomes impossible. Therefore, when the sample is plasma or the like, the degree of dilution is usually 5 to 20 times, preferably about 8 to about 12 times.

As the solution or solutions used in the above method 1), i.e., the solution containing the surfactant(s) and the ET-inhibiting peptide or the solutions containing them respectively, an aqueous solution of the above-exemplified surfactant(s) and ET-inhibiting peptide or aqueous solutions of them respectively are prepared so as to have a proper concentrations(s), and are used preferably after confirming that the aqueous solution(s) does not activate AL solution and neither enhance nor inhibits the reaction in the Limulus test. The solution containing the surfactant(s) and the ET-inhibiting peptide or the solutions containing them respectively may be autoclaved at 121° C. for 20 minutes for sterilization. Although the concentration of the surfactant(s) in the solution is not critical so long as it is in a range in which the final concentration of the surfactant(s) in a dilution obtained by diluting an objective sample with the solution(s) is in the range described above, it is usually 0.01 to 10 w/v %, preferably 0.1 to 5 w/v %, more preferably 0.2 to 2 w/v %, in view of ease of operations. Although the concentration of the ET-inhibiting peptide in the solution is not critical so long as it is in a range in which the final concentration of the ET-inhibiting peptide in a dilution obtained by diluting an objective sample with the solution(s) is in the range described above, it is usually 0.00002 to 0.2 w/v %, preferably 0.0002 to 0.1 w/v %, more preferably 0.002 to 0.02 w/v %, in view of ease of operations.

The AL solution containing predetermined amounts of the surfactant(s) and the ET-inhibiting peptide which is used in the above method 2) can, of course, be once freeze-dried, stored in the form of a reagent, redissolved in water containing no AL solution activating substance, such as distilled water for injection, and then used.

Since the inhibiting process of this invention makes it possible to inhibit ET activity in a sample completely by simultaneous use of small amounts of the surfactant(s) and the ET-inhibiting peptide, said process is very economical. A sample treated by the inhibiting process of this invention has low contents of the surfactant(s) and the ET-inhibiting peptide and hence can be used as a sample for measuring an ET analogous substance by utilization of Limulus test, without considering the influences of the surfactant(s) and the ET-inhibiting peptide on Limulus test.

Depending on the kind (source) of ET, its ET activity can be sufficiently inhibited using a low concentration of the ET-inhibiting peptide alone. Such inhibition is possible, for example, in the case of ET derived from *E. coli* 0127:B8. However, when the inhibition of ET activity is necessary for measuring an ET analogous substance in a sample in which it is not clear what kind of ET is contained, application of the inhibiting process of this invention is, of course, preferable.

The process for inhibiting ET activity of the present invention can be applied, for example, in the following fields.

In the case of measuring the amount of ET analogous substance such as β-glucan (more precisely (1→3)-β-D-glucan) in a sample using the Limulus test, the ET activity inhibiting process can be used to inhibit influences of endotoxin present in the sample on the results of measurement.

Further, in the case of measuring endotoxin or endotoxin analogous substance such as β-glucan in a sample by adding an AL solution to the sample to bring about the activation of the AL solution, followed by addition of a synthetic substrate thereto, the ET activity inhibiting process can be used to remove contamination of used reagents such as a synthetic substrate with endotoxin.

In addition, in an experiment using cultured cells, etc., when the cultured cells are susceptible to influences of endotoxin, the ET activity inhibiting process can be used to remove the contamination of used reagents with endotoxin.

To measure an ET analogous substance in a sample treated by the inhibiting process of this invention, it is sufficient that the measurement is carried out by a conventional method using AL solution, for example, the so-called Limulus test, i.e., a kinetic turbidimetric technique using an apparatus for exclusive use, such as Toxinometer ET-201 (mfd. by Wako Pure Chemical Industries, Ltd.), Toxinometer MT-251 (mfd. by Wako Pure Chemical Industries, Ltd.), LAL-5000 [mfd. by Associates of Cape Cod Inc. (ACC)] or the like; a chromogenic technique comprising measuring protease activity which arises owing to the activation of AL solution, by use of a synthetic substrate; or a gel-clot technique comprising judging whether a gel is produced by the activation of AL solution or not with the naked eye.

The ET analogous substance according to this invention is not critical so long as it is other than ET and reacts with AL solution to cause enzyme activation reaction or gelation reaction. Typical examples of the ET analogous substance are $(1\rightarrow 3)$-β-D-glucan and derivatives thereof. As the $(1\rightarrow 3)$-β-D-glucan and derivatives thereof, any polysaccharides can be exemplified without particular limitation so long as they contain $(1\rightarrow 3)$-β-D-glucoside linkage. Preferable examples of the $(1\rightarrow 3)$-β-D-glucan are natural polysaccharides obtained from cell walls or other components of, for example, various bacteria (e.g. Alcaligenes genus, Agrobacterium genus, etc.), yeasts (e.g. Saccharomyces genus, Candida genus, Crytrococcus genus, Trichosporon genus, Rhodotorula genus, etc.), molds (e.g. Aspergillus genus, Mucor genus, Penicillium genus, Trichophyron genus, Sporothrix genus, Phialophora genus, etc.), actinomycetes (Actinomyces genus, Nocardia genus, etc.), and mushrooms (e.g. *Cortinellus shiitake, Schizophyrum commune, Coriolus versicolor*, etc.), specific examples of the natural polysaccharides being curdlan, pachyman, sclerotan, lentinan, schizophyllan, coriolan, etc.; storage polysaccharides of algae, e.g. brown algae, Euglena, diatoms, etc., specific examples of the storage polysaccharides being laminaran, paramylon, etc. Preferable examples of the $(1\rightarrow 3)$-β-D-glucan derivatives are polysaccharide derivatives obtained by introducing at least one group selected from the group consisting of a sulphonic group, carboxymethyl group, carboxyethyl group, methyl group, hydroxyethyl group, hydroxy propyl group, sulfopropyl group, etc. into the natural polysaccharides or the storage polysaccharides according to a conventional method, for instance, any of the methods described, for example, in Munio Kotake "Daiyukikagaku" vol. 19, 7th ed. Asakura Shoten, May 10, 1967, pp. 70–101; A. E. Clarke et al., Phytochemistry, vol. 1, 175–188 (1967); and T. Sasaki et al. Europ. J. Cancer, vol. 15, 211–215 (1967).

The AL solution usable in this invention is not critical so long as it can be used for usual measurement of ET. There may be used AL solutions prepared from freeze-dried products of AL solutions which are commercially available, for example, from Associates of Cape Cod Inc. (ACC), HAEMACHEM, Inc., Biowhittaker Inc., Endosafe Inc., Teikoku Hormon Mfg. Co., Ltd., and Seikagaku Kogyo Co., Ltd. In addition, there can be exemplified any AL solution without particular limitation so long as it is prepared from hemocytes of horseshoe crab belonging to Limulus genus, Tachypleus genus or Carcinoscorpius genus and react with an AL solution activating substance to undergo enzyme (protease or the like) activation or gelation reaction.

This invention is illustrated below in further detail with reference to Examples, which are not by way of limitation but by way of illustration.

EXAMPLE 1

Reagents

ET solutions

There were used solutions prepared by weighing 10 mg of *Escherichia coli* (*E. coli*) 055:B5 LPS (available from Difco Laboratories), dissolving the same in 10 ml of distilled water for injection to prepare a 1 mg/ml solution as a starting solution, and diluting the starting solution properly with distilled water for injection.

AL solution

A freeze-dried product of AL solution derived from horseshoe crab belonging to Limulus genus (hereinafter the freeze-dried product being abbreviated as "LAL"; available from Wako Pure Chemical Industries, Ltd.; for dissolution in 2 ml) was dissolved in a buffer solution for LAL reconstitution (HS) (mfd. by Wako Pure Chemical Industries, Ltd.), and the LAL solution thus obtained was used as AL solution.

Aqueous surfactant solutions

Polyoxyethylene glycol p-t-octylphenyl ether (a nonionic surfactant, mfd. by Wako Pure Chemical Industries, Ltd.) was diluted to 10 w/v % with distilled water for injection, and the resulting dilution was autoclaved at 121° C. for 20 minutes to obtain a starting solution. The starting solution was properly diluted with distilled water for injection, and the thus obtained diluted solutions were used as aqueous surfactant solutions after confirming that they did not activate the AL solution and neither inhibited nor enhance the reaction for measuring βG by the Limulus test.

Aqueous polymyxin B (hereinafter abbreviated as "Px B") solutions

Px B sulfate (mfd. by Wako Pure Chemical Industries, Ltd.) was diluted to 1.0 w/v % with distilled water for injection, and the resulting dilution was autoclaved at 121° C. for 20 minutes to obtain a starting solution. The starting solution was properly diluted with distilled water for injection (or 0.2 w/v % aqueous surfactant solution prepared in the above), and the thus obtained dilutions were used as aqueous Px B solutions after confirming that they did not activate the AL solution and neither inhibited nor enhance the reaction for measuring βG by the Limulus test.

Procedure

To 2.0 ml of normal human heparinized plasma was added 20 μl of ET solution having a predetermined concentration, and 100 μl of the resulting ET spiked plasma was diluted 10 times (i.e. 1/10) with 900 μl of distilled water for injection, each of aqueous Px B solutions having predetermined concentrations, or each of aqueous surfactant solutions having predetermined concentrations. Each of the thus obtained dilutions was heat-treated at 80° C. for 5 minutes and then immediately cooled with ice (the final concentrations of ET, Px B and the surfactant were 2 ng/ml, 0.0018 to 0.009 w/v % and 0.09 to 0.45 w/v %, respectively). The ET concentration in the diluted plasma thus obtained was measured as follows by a conventional method using an apparatus "Toxinometer MT-251" (mfd. by Wako Pure Chemical Industries, Ltd.).

To 0.1 ml of the LAL solution was added 0.1 ml of the aforesaid diluted plasma, and stirred, after which a time required for reducing the transmittance of the resulting mixture by 5% (hereinafter abbreviated as "Tg") was measured while maintaining the temperature at 37° C. The ET concentration in the diluted plasma was determined on the basis of the thus obtained Tg value by use of a calibration curve showing the relationship between ET concentration and Tg which had been previously obtained by carrying out the same measurement as described above except for using ET solutions having various known concentrations in place of the samples.

Results

Figure 2:
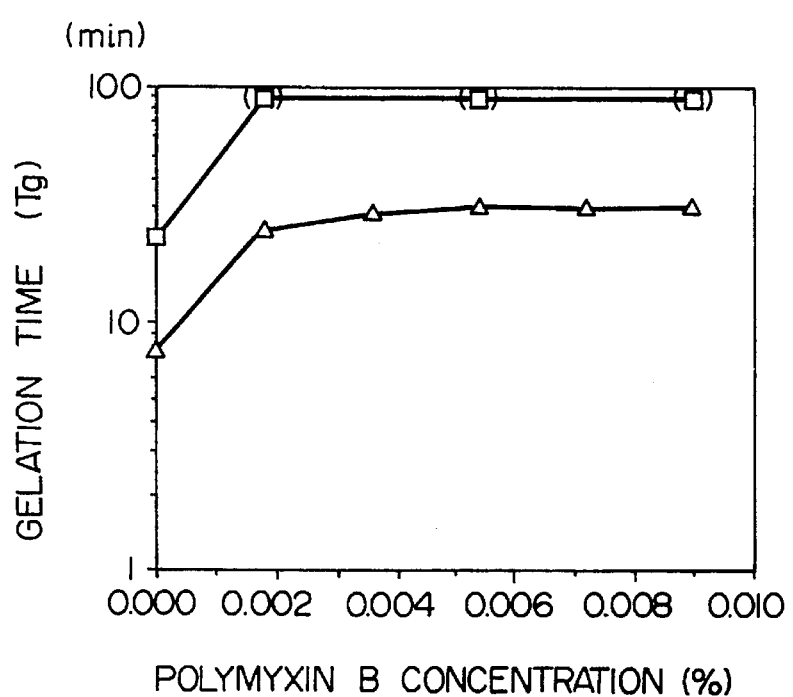
FIG. 2 is a graph showing the influence of the concentration of polymyxin B (hereinafter abbreviated as "Px B") on the measurement of ET (*E. coli* 055:B5 LPS) in plasma, which was obtained in Example 1.

FIGS. 1 and 2 show the results obtained. FIG. 1 shows the results obtained for the plasma diluted with each surfactant solution and is a graph obtained by plotting the gelation time (Tg) of the diluted and heated plasma on the axis of ordinate corresponding to individual surfactant concentrations (at the time of the heat treatment) on the axis of abscissa. FIG. 2 shows the results obtained for the plasma diluted with each Px B solution and is a graph obtained by plotting the gelation time (Tg) of the diluted and heated plasma on the axis of ordinate corresponding to individual Px B concentrations (at the time of the heat treatment) on the axis of abscissa. In FIG. 2, -Δ- shows the results obtained by use of the aqueous solutions containing Px B alone, and -□- shows the results obtained by use of the aqueous solutions containing both Px B and 0.2 w/v % of the surfactant (polyoxyethylene glycol p-t-octylphenyl ether) (the surfactant concentration at the time of the heat treatment was 0.18 w/v %). In FIG. 2, (□) indicates that Tg was 90 minutes or more, in other words, ET was not detected.

As is clear from the results shown in FIG. 1, the Tg value obtained from the plasma diluted with distilled water for injection was 7.8 minutes, while the Tg values obtained from the plasma diluted with each of 0.1 to 0.5% aqueous surfactant solutions (the surfactant concentration at the time of the heat treatment was 0.09 to 0.45%) was as large as 16.3 to 33.7 minutes, indicating that the ability of ET to activate AL solution (ET activity) was deteriorated (the smaller Tg, the higher the ET activity). As is clear from the results shown in FIG. 2, the Tg value obtained from the plasma diluted with distilled water for injection was 7.8 minutes, while the Tg values obtained from the plasma diluted with each of 0.002 to 0.01 w/v % aqueous Px B solutions (the Px B concentration at the time of the heat treatment was 0.0018 to 0.009 w/v %) was as large as 24.2 to 32.9 minutes, indicating that the ET activity was lowered. Further, from the results shown in FIG. 2, it can be seen that when plasma was diluted with aqueous solution containing both 0.002 to 0.01 w/v % of Px B and 0.2% of the surfactant (the concentrations of the surfactant and Px B at the time of the heat treatment were 0.18% and 0.0018 to 0.009 w/v %, respectively), ET was not detected (Tg became 90 minutes or more).

As is clear from the results described above, the ET activity of *E. coli* 0.55:B5 LPS spiked to plasma is completely inhibited by the simultaneous presence of the surfactant and Px B.

EXAMPLE 2

Reagents

The same AL solution, aqueous surfactant solutions and aqueous Px B solutions as described in Example 1 were used.

ET solutions

There were used solutions prepared by weighing 10 mg of *E. coli* 0111:B4 LPS (available from Difco Laboratories), dissolving the same in 10 ml of distilled water for injection to prepare a 1 mg/ml solution as a starting solution, and diluting the starting solution properly with distilled water for injection.

Procedure

To 0.6 ml of normal human heparinized plasma was added 12 μl of ET solution having a predetermined concentration, and 100 μl of the resulting ET spiked plasma was diluted 10 times with 900 μl of distilled water for injection, 0.04 w/v % aqueous surfactant solution, 0.2 w/v % aqueous surfactant solution, or 0.01 w/v % aqueous Px B solution [containing 0.2 w/v % of the surfactant (polyoxyethylene glycol p-t-octylphenyl ether)], respectively. Each of the thus obtained dilutions was heat-treated at 80° C. for 5 minutes and then immediately cooled with ice (the final concentration of ET was 1.96 ng/ml). The ET concentration in the diluted plasma thus obtained was measured in the same manner as in Example 1.

Results

The results obtained are shown in Table 1.

TABLE 1

| Diluent | Tg (min) | Concentration (pg/ml) |
|---|---|---|
| Distilled water for injection | 10.0 | 289.1 |
| 0.04% Aqueous surfactant solution | 6.3 | 2363.0 |
| 0.2% Aqueous surfactant solution | 40.4 | 3.4 |
| 0.01% Aqueous Px B solution (containing 0.2% of the surfactant) | >90 | — |

As is clear from the results shown in Table 1, the Tg value obtained from the plasma diluted with distilled water for injection was 10.0 minutes, while the Tg value obtained from the plasma diluted with the 0.2 w/v % aqueous surfactant solution (the surfactant concentration at the time of the heat treatment was 0.18 w/v %) was as large as 40.4 minutes, indicating that the ET activity was lowered. It can also be seen that when plasma was diluted with the 0.01 w/v % aqueous Px B solution (containing 0.2 w/v % of the surfactant) (the concentrations of Px B and the surfactant at the time of the heat treatment were 0.009 w/v % and 0.18 w/v %, respectively), ET was not detected (Tg became 90 minutes or more). In the case of the plasma diluted with the 0.04% aqueous surfactant solution, the Tg value was smaller (the ET activity was higher) than in the case of the plasma diluted with distilled water for injection. The reason can be presumed as follows: the influence of factors capable of inhibiting the reaction of ET with AL solution which were present in plasma was reduced by the addition of the surfactant.

As is clear from the results described above, the ET activity of *E. coli* 0.111:B4 LPS spiked to plasma is completely inhibited by the simultaneous presence of the surfactant and Px B.

EXAMPLE 3

Reagents

The same AL solution, aqueous surfactant solutions and aqueous Px B solutions as described in Example 1 were used.

ET solutions

There were used solutions prepared by weighing 10 mg of *E. coli* 0127:B8 LPS (available from Difco Laboratories), dissolving the same in 10 ml of distilled water for injection to prepare a 1 mg/ml solution as a starting solution, and diluting the starting solution properly with distilled water for injection.

Procedure

To 0.7 ml of normal human heparinized plasma was added 14 µl of ET solution having a predetermined concentration, and 100 µl of the resulting ET spiked plasma was diluted 10 times with 900 µl of distilled water for injection, 0.04 w/v % aqueous surfactant solution, 0.2 w/v % aqueous surfactant solution, 0.01 w/v % aqueous Px B solution, or 0.01 w/v % aqueous Px B solution containing 0.2 w/v % of the surfactant (polyoxyethylene glycol p-t-octylphenyl ether), respectively. Each of the thus obtained diluted solutions was heat-treated at 80° C. for 5 minutes and then immediately cooled with ice (the final concentration of ET was 1.96 ng/ml). The ET concentration in the diluted plasma thus obtained was measured in the same manner as in Example 1.

Results

The results obtained are shown in Table 2.

TABLE 2

| Diluent | Tg (min) | Concentration (pg/ml) |
| --- | --- | --- |
| Distilled water for injection | 10.0 | 221.2 |
| 0.04% Aqueous surfactant solution | 6.6 | 2152.0 |
| 0.2% Aqueous surfactant solution | 28.6 | 6.3 |
| 0.01% Aqueous Px B solution | >90 | — |
| 0.01% Aqueous Px B solution (containing 0.2% of the surfactant) | >90 | — |

As is clear from the results shown in Table 2, the Tg value obtained from the plasma diluted with distilled water for injection was 10.6 minutes, while the Tg value obtained from the plasma diluted with the 0.2 w/v % aqueous surfactant solution (the surfactant concentration at the time of the heat treatment was 0.18 w/v %) was as large as 28.6 minutes, indicating that the ET activity was lowered. It can also be seen that when plasma was diluted with the 0.01 w/v % aqueous Px B solution or the 0.01 w/v % aqueous Px B solution containing 0.2 w/v % of the surfactant (the concentrations of Px B and the surfactant at the time of the heat treatment were 0.009 w/v % and 0.18 w/v %, respectively), ET was not detected (Tg became 90 minutes or more). In the case of the plasma diluted with the 0.04% aqueous surfactant solution, the Tg value was smaller (the ET activity was higher) than in the case of the plasma diluted with distilled water for injection. The reason can be presumed as follows: the influence of factors capable of inhibiting the reaction of ET with AL solution which were present in plasma was reduced by the addition of the surfactant.

As is clear from the results described above, the ET activity of *E. coli* 0.127:B8 LPS spiked to plasma is completely inhibited by the simultaneous presence of the surfactant and Px B.

EXAMPLE 4

Reagents

The same AL solution, aqueous surfactant solutions and aqueous Px B solutions as described in Example 1 were used.

ET solutions

There were used solutions prepared by weighing 10 mg of *E. coli* 0128:B12 LPS (available from Difco Laboratories), dissolving the same in 10 ml of distilled water for injection to prepare a 1 mg/ml solution as a starting solution, and diluting the starting solution properly with distilled water for injection.

Procedure

To 1.3 ml of normal human heparinized plasma was added 13 µl of ET solution having a predetermined concentration, and 100 µl of the resulting ET spiked plasma was diluted 10 times with 900 µl of distilled water for injection, each of aqueous surfactant solutions having predetermined concentrations, each of aqueous Px B solutions having predetermined concentrations, or each of aqueous Px B solutions having predetermined concentrations and containing 0.1 w/v % or 0.2 w/v % of the surfactant (polyoxyethylene glycol p-t-octylphenyl ether), respectively. Each of the thus obtained dilutions was heat-treated at 80° C. for 5 minutes and then immediately cooled with ice (the final concentrations of ET, Px B and the surfactant were 2 ng/ml, 0.00009 to 0.009 w/v %, and 0.09 to 0.9 w/v %, respectively). The ET concentration in the diluted plasma thus obtained was measured in the same manner as in Example 1.

Results

Figure 3:
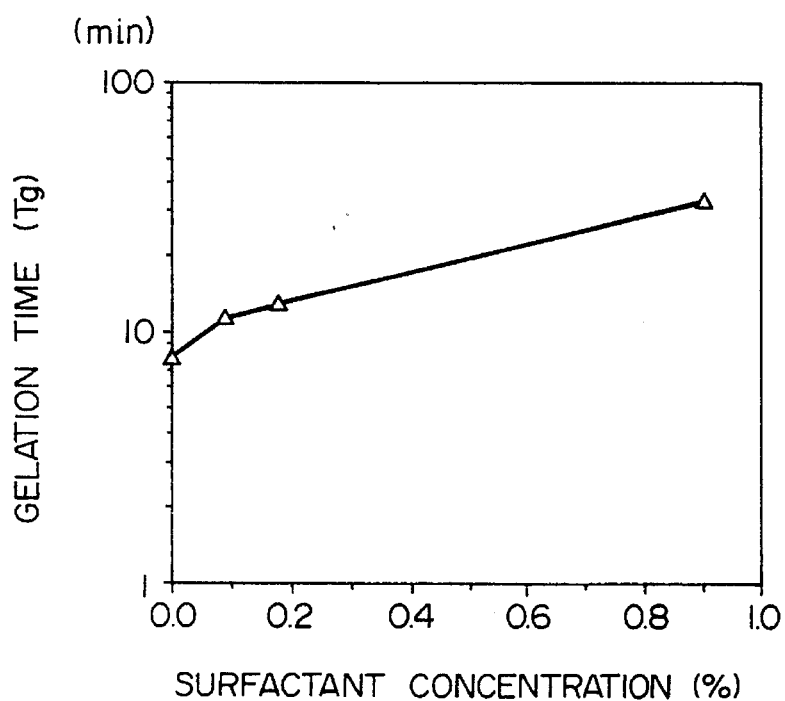
FIG. 3 is a graph showing the influence of the concentration of the surfactant on the measurement of ET (*E. coli* 0128:B12 LPS) in plasma, which was obtained in Example 4.
Figure 4:
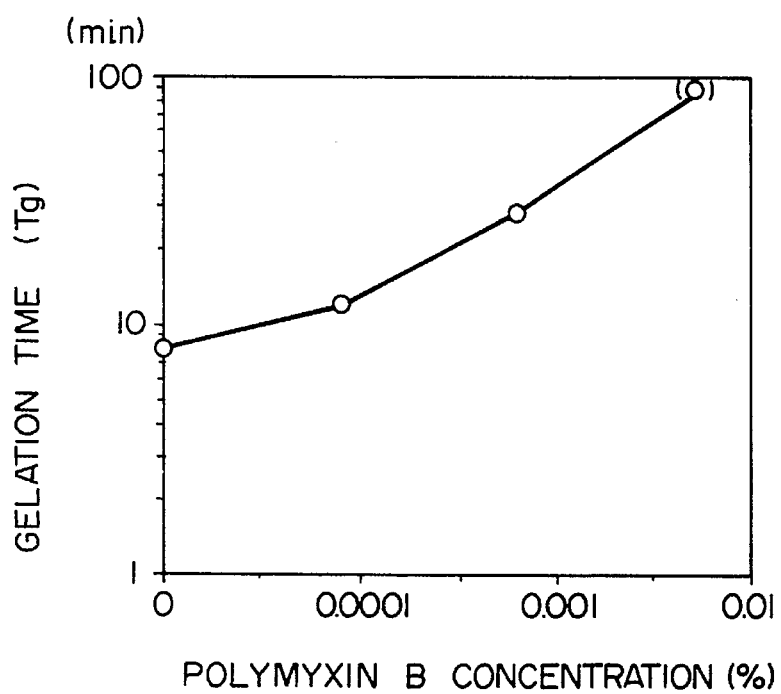
FIG. 4 is a graph showing the influence of the concentration of Px B on the measurement of ET (*E. coli* 0128:B12 LPS) in plasma, which was obtained in Example 4.
Figure 5:
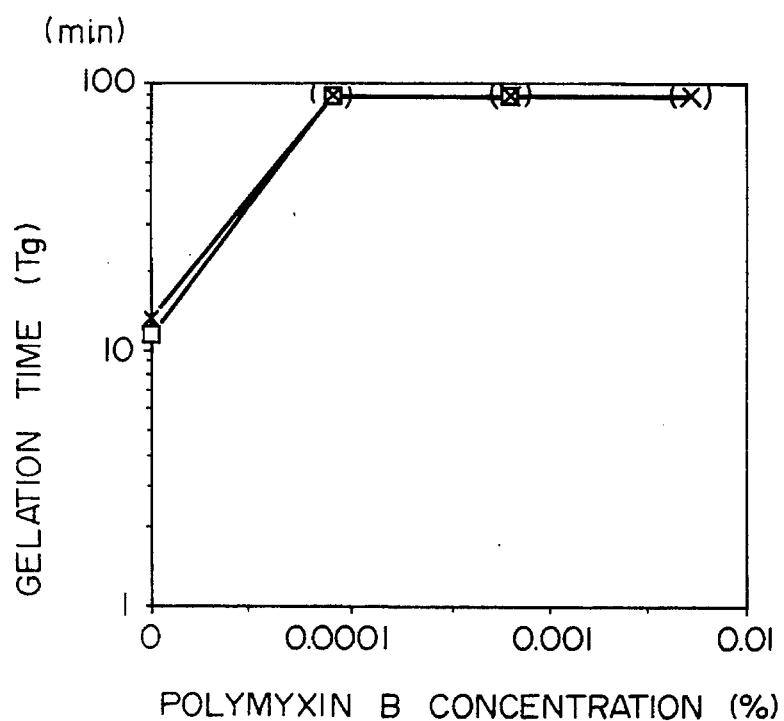
FIG. 5 is a graph showing the influence of the concentration of Px B on the measurement of ET (*E. coli* 0128:B12 LPS) in plasma in the presence of the surfactant, which was obtained in Example 4.

FIGS. 3 to 5 show the results obtained. FIG. 3 shows the results obtained from the plasma diluted with each surfactant solution and is a graph obtained by plotting the gelation time (Tg) of the diluted and heated plasma on the axis of ordinate corresponding to individual surfactant concentrations (at the time of the heat treatment) on the axis of abscissa. FIG. 4 shows the results obtained from the plasma diluted with each Px B solution and is a graph obtained by plotting the gelation time (Tg) of the diluted and heated plasma on the axis of ordinate corresponding to individual Px B concentrations (at the time of the heat treatment) on the axis of abscissa. FIG. 5 shows the results obtained from the plasma diluted with each aqueous solution containing the surfactant and Px B and is a graph obtained by plotting the gelation time (Tg) of the diluted and heated plasma on the axis of ordinate corresponding to individual Px B concentrations (at the time of the heat treatment) on the axis of abscissa. In FIG. 5, -□- shows the results obtained by use of aqueous solutions containing 0.1 w/v % of the surfactant (the surfactant concentration at the time of the heat treatment was 0.09 w/v %), and -x- shows the results obtained by use of aqueous solutions containing 0.2 w/v % of the surfactant (the surfactant concentration at the time of the heat treatment was 0.18 w/v %). All of (o) in FIG. 4 and (□) and (x) in FIG. 5 indicate that Tg was 90 minutes or more, in other words, ET was not detected.

As is clear from the results shown in FIGS. 3 to 5, the ET activity in plasma can be completely inhibited by the presence of 0.009 w/v % of Px B or the simultaneous presence of the surfactant and Px B. It can also be seen that when the ET activity is inhibited by the inhibiting process of this invention, the amount of Px B used can be reduced (to one hundredth that required in the case of using Px B alone), in other words, the process of this invention is economically superior to conventional processes using Px B alone.

EXAMPLE 5

Reagents

The same AL solution, aqueous surfactant solutions and aqueous Px B solutions as described in Example 1 were used.

ET solutions

There were used solutions prepared by weighing 10 mg of *Salmonella typhimurium* LPS (available from Difco Laboratories), dissolving the same in 10 ml of distilled water for injection to prepare a 1 mg/ml solution as a starting solution, and diluting the starting solution properly with distilled water for injection.

Procedure

To 1.0 ml of normal human heparinized plasma was added 10 μl of ET solution having a predetermined concentration, and 100 μl of the resulting ET spiked plasma was diluted 10 times with 900 μl of distilled water for injection, 0.2 w/v % aqueous surfactant solution, 0.01 w/v % aqueous Px B solution, or 0.01 w/v % aqueous Px B solution containing 0.2 w/v % of the surfactant (polyoxyethylene glycol p-t-octylphenyl ether), respectively. Each of the thus obtained dilutions was heat-treated at 80° C. for 5 minutes and then immediately cooled with ice (the final concentration of ET was 2 ng/ml). The ET concentration in the diluted plasma thus obtained was measured in the same manner as in Example 1.

Results

The results obtained are shown in Table 3.

TABLE 3

| Diluent | Tg (min) | Concentration (pg/ml) |
|---|---|---|
| Distilled water for injection | 8.2 | 453.6 |
| 0.2% Aqueous surfactant solution | 12.3 | 77.9 |
| 0.01% Aqueous Px B solution | 13.4 | 55.7 |
| 0.01% Aqueous Px B solution (containing 0.2% of the surfactant) | >90 | — |

As is clear from the results shown in Table 3, the ET activity of *S. typhimurium* LPS spiked to plasma is completely inhibited by the simultaneous presence of the surfactant and Px B.

EXAMPLE 6

Reagents

The same AL solution, aqueous surfactant solutions and aqueous Px B solutions as described in Example 1 were used.

Aqueous β-glucan solutions

There were used solutions prepared by weighing 100 mg of carboxymethylated curdlan [a linear (1→3)-β-D-glucan derivative, mfd. by Wako Pure Chemical Industries, Ltd.], dissolving the same in 10 ml of distilled water for injection to prepare a 10 mg/ml solution as a starting solution, and diluting the starting solution properly with distilled water for injection.

Procedure

By diluting 100 μl of 50 ng/ml aqueous β-glucan solution 10 times with 900 μl of 0.2 w/v % aqueous surfactant solution, 0.01 w/v % aqueous Px B solution, or 0.01 w/v % aqueous Px B solution containing 0.2 w/v % of polyoxyethylene glycol p-t-octylphenyl ether, solutions containing spiked β-glucan (the final concentration of β-glucan was 5 ng/ml) were prepared. The β-glucan concentration in each of the prepared solutions was measured as follows by a conventional method using an apparatus "Toxinometer MT-251" (mfd. by Wako Pure Chemical Industries, Ltd.). To 0.1 ml of the LAL solution was added 0.1 ml of each of the above-mentioned diluted solutions, and stirred, after which a time required for reducing the transmittance of the resulting mixture by 5% (hereinafter abbreviated as "Tg") was measured while maintaining the temperature at 37° C. The β-glucan concentration was determined on the basis of the thus obtained Tg value by use of a calibration curve showing the relationship between β-glucan concentration and Tg which had been previously obtained by carrying out the same measurement as described above except for using β-glucan solutions various in their concentrations as samples. On the basis of the results of the measurement, the recovery of β-glucan was calculated.

Results

The results obtained are shown in Table 4.

TABLE 4

| Diluent | Recovery of β-glucan (%) |
|---|---|
| 0.2% Aqueous surfactant solution | 100 |
| 0.01% Aqueous Px B solution | 112 |
| 0.01% Aqueous Px B solution (containing 0.2% of the surfactant) | 88 |

As is clear from the results shown in Table 4, the recovery of β-glucan was as high as about 90% to about 110%, whichever diluted solution was used. Therefore, it can be seen that none of the diluted solutions either inhibit or enhance the reaction of AL solution with β-glucan.

EXAMPLE 7

Reagents

The same AL solution, aqueous surfactant solutions and aqueous Px B solutions as described in Example 1 were used.

ET solutions

There were used solutions prepared by weighing 10 mg of *E. coli* 026:B6 LPS (available from Difco Laboratories), dissolving the same in 10 ml of distilled water for injection to prepare a 1 mg/ml solution as a starting solution, and diluting the starting solution properly with distilled water for injection.

Aqueous surfactant solutions

Various aqueous surfactant solutions were prepared in the same manner as described in Example 1 except for using as surfactants, sodium deoxycholate (an anionic surfactant, mfd. by Wako Pure Chemical Industries, Ltd.), Emalgen 709 [a nonionic surfactant (a polyoxyethylene higher alcohol ether), a trade name, Kao Corp.] and Amphitol 20N (an amphoteric surfactant, a trade name, Kao Corp.; main constituent: lauryldimethylamine oxide).

Procedure

To 1.7 ml of normal human heparinized plasma was added 17 μl of ET solution having a predetermined concentration, and 100 μl of the resulting ET spiked plasma was diluted 10 times with 900 μl of distilled water for injection, 0.1 w/v % aqueous sodium deoxycholate solution, 0.2 w/v % aqueous Emalgen 709 solution, 0.4 w/v % aqueous Amphitol 20N solution, 0.01 w/v % aqueous Px B solution, 0.1 w/v % aqueous sodium deoxycholate solution containing 0.01 w/v % of Px B, 0.2 w/v % aqueous Emalgen 709 solution containing 0.01 w/v % of Px B, or 0.4 w/v % aqueous Amphitol 20N solution containing 0.01 w/v % of Px B. Each of the thus obtained diluted solutions was heat-treated at 80° C. for 5 minutes and then immediately cooled with ice (the final concentration of ET was 4 ng/ml). The ET concentration in the diluted plasma thus obtained was measured in the same manner as in Example 1.

Results

The results obtained are shown in Table 5.

TABLE 5

| Diluent | Tg (min) | Concentration (pg/ml) |
|---|---|---|
| Distilled water for injection | 9.0 | 1019.0 |
| 0.1% Aqueous sodium deoxycholate solution | 7.5 | 2287.0 |
| 0.2% Aqueous Emalgen 709 solution | 27.3 | 22.7 |
| 0.4% Aqueous Amphitol 20N solution | 52.6 | 4.3 |
| 0.01% Aqueous Px B solution | 30.8 | 16.2 |
| 0.1% Aqueous sodium deoxycholate solution (containing 0.01% of Px B) | >90 | — |
| 0.2% Aqueous Emalgen 709 solution (containing 0.01% of Px B) | >90 | — |
| 0.4% Aqueous Amphitol 20N solution (containing 0.01% of Px B) | >90 | — |

As is clear from the results shown in Table 5, the ET activity of *E. coli* 0.26:B6 LPS spiked to plasma is completely inhibited by the simultaneous presence of each surfactant and Px B.

EXAMPLE 8

Reagents

The same AL solution, aqueous surfactant solutions and aqueous Px B solutions as described in Example 1 were used.

Aqueous surfactant solutions

Various aqueous surfactant solutions were prepared in the same manner as described in Example 1 except for using as surfactants, polyoxyethylene glycol p-t-octylphenyl ether (a nonionic surfactant, mfd. by Wako Pure Chemical Industries, Ltd.), Emalgen 709 [a nonionic surfactant (a polyoxyethylene higher alcohol ether), a trade name, Kao Corp.] and Amphitol 20N (an amphoteric surfactant, a trade name, Kao Corp.; main constituent: lauryldimethylamine oxide).

ET solutions

There were used solutions prepared by weighing 10 mg of *Salmonella typhosa* 0901 LPS (available from Difco Laboratories), dissolving the same in 10 ml of distilled water for injection to prepare a 1 mg/ml solution as a starting solution, and diluting the starting solution properly with distilled water for injection.

Procedure

To 1.0 ml of normal human heparinized plasma was added 10 μl of ET solution having a predetermined concentration, and 100 μl of the resulting ET spiked plasma was diluted 10 times with 900 μl of distilled water for injection, 0.2 w/v % aqueous polyoxyethylene glycol p-t-octylphenyl ether solution containing 0.01 w/v % of Px B, 0.2 w/v % aqueous Emalgen 709 solution containing 0.01 w/v % of Px B, or 0.4 w/v % aqueous Amphitol 20N solution containing 0.01 w/v % of Px B. Each of the thus obtained diluted solutions was heat-treated at 80° C. for 5 minutes and then immediately cooled with ice (the final concentration of ET was 4 ng/ml). The ET concentration in the diluted plasma thus obtained was measured in the same manner as in Example 1.

Results

The results obtained are shown in Table 6.

TABLE 6

| Diluent | Tg (min) | Concentration (pg/ml) |
|---|---|---|
| Distilled water for injection | 7.8 | 910.9 |
| 0.2% Aqueous polyoxyethylene glycol p-t-octylphenyl ether solution (containing 0.01% of Px B) | >90 | — |
| 0.2% Aqueous Emalgen 709 solution (containing 0.01% of Px B) | >90 | — |
| 0.4% Aqueous Amphitol 20N solution (containing 0.01% of Px B) | >90 | — |

As is clear from the results shown in Table 6, the ET activity of *S. typhosa* 0901 LPS spiked to plasma is completely inhibited by the simultaneous presence of each surfactant and Px B.

EXAMPLE 9

Reagents

The same AL solution, aqueous surfactant solutions and aqueous Px B solutions as described in Example 1 were used.

Aqueous β-glucan solutions

After 108 mg of curdlan [a linear (1→3)-β-D-glucan derivative, mfd by Wako Pure Chemical Industries, Ltd.] was weighed, 10 ml of distilled water for injection and then 800 μl of 1N NaOH were added to dissolve the curdlan, whereby a 10 mg/ml solution was prepared. This solution was diluted 10 times with distilled water for injection to obtain a starting solution, which was properly diluted with distilled water for injection. The thus obtained solutions were used as aqueous β-glucan solutions.

Procedure

By diluting 100 μl of 10 ng/ml aqueous β-glucan solution 10 times with 900 μl of each of aqueous surfactant solutions having predetermined concentrations and containing 0.01 w/v % of Px B, there were prepared solutions containing spiked β-glucan (the final concentration of β-glucan was 1 ng/ml, and the final concentrations of Px B and the surfactant in the β-glucan spiked solutions were 0.009 w/v % and 0.9 to 4.5 w/v %, respectively). The recovery of β-glucan from the various β-glucan spiked solutions was determined in the same manner as described in Example 6.

Results

Figure 6:
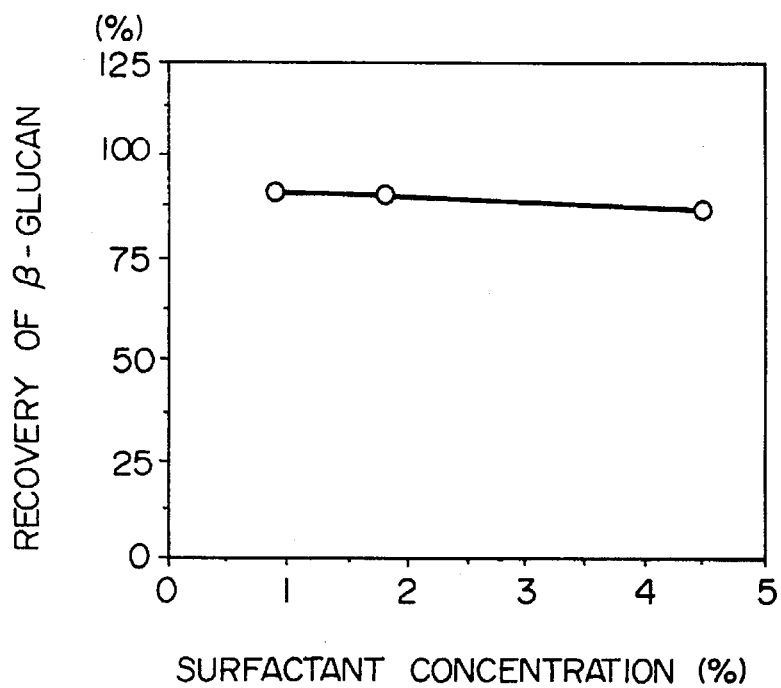
FIG. 6 is a graph showing the influence of the concentration of the surfactant on the measurement of β-glucan in the presence of Px B, which was obtained in Example 9.

The results obtained are shown in FIG. 6. FIG. 6 is a graph obtained by plotting the recovery of β-glucan on the axis of ordinate corresponding to individual surfactant concentrations (in the β-glucan spiked solutions containing 0.009 w/v % of Px B) on the axis of abscissa.

As is clear from the results shown in FIG. 6, the recovery of β-glucan was kept constant at about 90% even when the surfactant concentration was increased. From this fact, it can be judged that in the above surfactant concentration range, the surfactant (polyoxyethylene glycol p-t-octylphenyl ether) neither inhibits nor enhance the reaction of AL solution with β-glucan.

EXAMPLE 10

Reagents

There were used the same AL solution, aqueous surfactant solutions and aqueous Px B solutions as described in Example 1.

Procedure

By diluting 100 μl of ET solution having a predetermined concentration 10 time with 900 μl of distilled water for injection, 0.2 w/v % aqueous surfactant (polyoxyethylene glycol p-t-octylphenyl ether) solution, each of 0.002 to 0.01 w/v % aqueous Px B solutions, or each of 0.2 w/v % aqueous surfactant (polyoxyethylene glycol p-t-octylphenyl ether) solutions containing 0.002 to 0.01 w/v % of Px B, there were prepared solutions containing spiked ET (the final concentration of ET was 2 ng/ml, and the final concentrations of Px B and the surfactant in the ET spiked solutions were 0.0018 to 0.009 w/v % and 0.18 w/v %, respectively). The ET concentration in the ET spiked solutions was measured in the same manner as in Example 1.

Results

Figure 7:
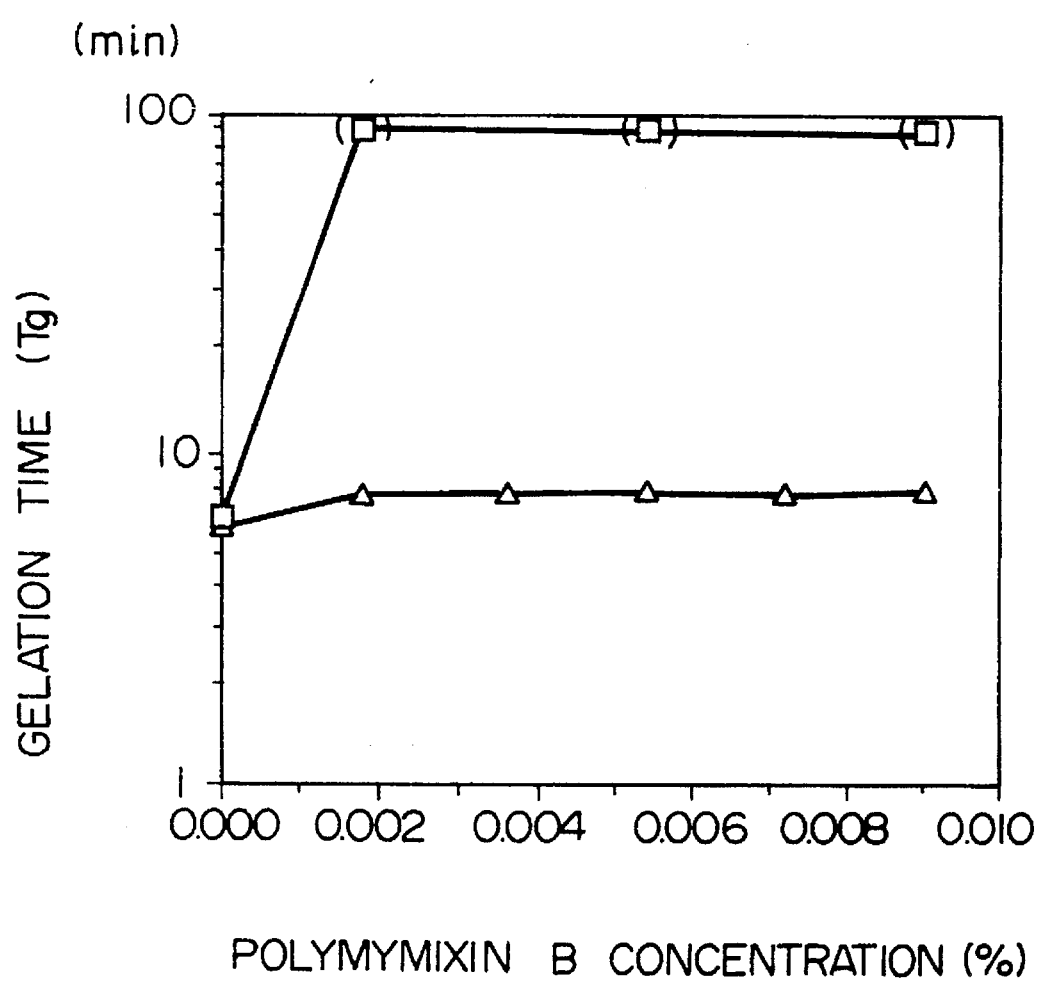
FIG. 7 is a graph showing the influence of the concentration of Px B on the measurement of the ET concentration in an aqueous solution containing ET (*E. coli* 055:B5 LPS), which was obtained in Example 10.

The results obtained are shown in FIG. 7. FIG. 7 is a graph obtained by plotting the gelation time (Tg) of the ET spiked solutions on the axis of ordinate corresponding to individual Px B concentrations in the ET spiked solutions on the axis of abscissa. In FIG. 7, -△- shows the results obtained for the ET spiked solutions prepared by use of the aqueous Px B solutions various in their concentrations, and -□- shows the results obtained for the ET spiked solutions prepared by use of the aqueous Px B solutions containing 0.2 w/v % of the surfactant.

As is clear from the results shown in FIG. 7, the ET activity of E. coli 0.55:B5 LPS in the ET spiked solutions is completely inhibited by the simultaneous presence of the surfactant and Px B.

EXAMPLE 11

Reagents

There were used the same AL solution, aqueous surfactant solutions and aqueous Px B solutions as described in Example 1, the same ET solutions as described in Example 8, and the same β-glucan solutions as described in Example 9.

Procedure

To 1.0 ml of normal human heparinized plasma was added 10 μl of 4 g/ml ET solution and 10 μl or 100 ng/ml β-glucan solution, and 100 μl of the obtained plasma containing spiked ET and spiked β-glucan was diluted 10 times with 900 μl of distilled water for injection, 0.2 w/v % aqueous surfactant (polyoxyethylene glycol p-t-octylphenyl ether) solution, 0.01 w/v % aqueous Px B solution, or 0.2 w/v % aqueous surfactant (polyoxyethylene glycol p-t-octylphenyl ether) solution containing 0.01 w/v % of Px B. Each of the thus obtained diluted solutions was heat-treated at 80° C. for 5 minutes and then immediately cooled with ice (the final concentrations of ET and β-glucan were 3.92 ng/ml and 196 pg/ml). The β-glucan concentration in the diluted plasma thus obtained was measured in the same manner as in Example 6. The same procedure as described above was carried out for a mixture prepared by adding 10 μl of distilled water for injection and 10 μl of 20 ng/ml β-glucan solution to the same plasma as used in the above, and the β-glucan concentration in the mixture was measured.

Further, on the basis of the measurement results, the recovery of β-glucan was calculated.

Results

The results obtained are shown in Table 7.

TABLE 7

| | Recovery of β-glucan (%) | |
|---|---|---|
| Diluent | ET spiked plasma | Plasma without spiked ET |
| Distilled water for injection | 54200 | 107 |
| 0.2% Aqueous surfactant solution | 3540 | 98 |
| 0.01% Aqueous Px B solution | 893 | 105 |
| 0.01% Aqueous Px B solution (containing 0.2% of the surfactant) | 117 | 112 |

As is clear from the results shown in Table 7, β-glucan can be measured without the influence (the influence of causing positive errors in measured values) of ET present in a sample only when the surfactant and Px B are present during the measurement of β-glucan.

As is clear from the above, this invention provides a process for inhibiting ET activity in a sample effectively. The process of this invention is effective in that it permits easier and more certain inhibition of ET activity than do conventional processes, so that it makes it possible to measure an ET analogous substance without the influence of ET. Therefore, this invention contributes greatly to the art.

What is claimed is:

1. A process for selectively inhibiting the activity of an endotoxin which comprises contacting a) a surfactant and b) an endotoxin-inhibiting peptide selected from the group consisting of polymyxins A, B, C, D, E, K, M and P, tachyplesin, polyphemusin and anti-LPS factor, which binds to the endotoxin to inhibit the reaction of the endotoxin with c) a sample containing the endotoxin.

2. A process according to claim 1, wherein the mixture is heated.

3. A process according to claim 2, wherein the mixture is heated at 60°–220° C. for 3 to 60 minutes.

4. A process according to claim 1, wherein the concentration of the surfactant is 0.005 to 5.0 w/v % and the concentration of the endotoxin-inhibiting peptide is 0.00001 to 0.1 w/v %.

5. A process according to claim 1, wherein the endotoxin-inhibiting peptide is polymyxin B.

6. A process according to claim 1, wherein the surfactant is a nonionic surfactant or an amphoteric surfactant.

* * * * *